(12) United States Patent
Thiem

(10) Patent No.: US 7,357,384 B2
(45) Date of Patent: Apr. 15, 2008

(54) ORIENTABLE SAMPLE HOLDER HAVING A ZERO-POINT INDICATION, FOR A MICROTOME

(75) Inventor: Stefan Thiem, Heidelberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 436 days.

(21) Appl. No.: 10/847,272

(22) Filed: May 17, 2004

(65) Prior Publication Data

US 2004/0239024 A1 Dec. 2, 2004

(30) Foreign Application Priority Data

May 28, 2003 (DE) ............... 103 24 696

(51) Int. Cl.
*B23Q 3/16* (2006.01)
*B23Q 1/25* (2006.01)
(52) U.S. Cl. .................. 269/60; 83/915.5
(58) Field of Classification Search .......... 83/915.5; 269/60
See application file for complete search history.

(56) References Cited

U.S. PATENT DOCUMENTS 3,771,405 A * 11/1973 Blum .................. 83/714
3,788,633 A * 1/1974 Cho .................... 269/60
5,782,572 A 7/1998 Thiem
6,254,075 B1 * 7/2001 Kozima ................ 269/73

FOREIGN PATENT DOCUMENTS

| DE | 82 17 700 U1 | 12/1982 |
|---|---|---|
| DE | 3615714 A1 | 11/1987 |
| DE | 196 04 001 C2 | 8/1997 |
| GB | 2044931 A | 10/1980 |
| GB | 1437909 A | 1/2000 |

* cited by examiner

*Primary Examiner*—Kenneth E. Peterson
*Assistant Examiner*—Sean Michalski
(74) *Attorney, Agent, or Firm*—Hodgson Russ LLP

(57) ABSTRACT

A device for signaling the position of an orientable sample holder for a microtome is described. The drive system (2) for moving the sample holder is arranged in a housing. At least one rotatably mounted spindle (4), and a nut (5) running on the spindle (4), are provided for moving the sample holder in one spatial direction. The nut (5) comprises a position element (6) identifying the zero position, and an indicating element (11) is associated with the position element (6).

5 Claims, 5 Drawing Sheets

ORIENTABLE SAMPLE HOLDER HAVING A ZERO-POINT INDICATION, FOR A MICROTOME

CROSS REFERENCE TO RELATED APPLICATIONS

This application claims priority of the German patent application 103 24 696.7 filed May 28, 2003 which is incorporated by reference herein.

FIELD OF THE INVENTION

The invention concerns microtomes, and more particularly a device for signaling the position of an orientable sample holder for a microtome.

BACKGROUND OF THE INVENTION

DE 82 17 700 U1 discloses a specimen head, displaceable in two spatial directions, that is enclosed by a bracket. Displacement of the bracket is accomplished via two link elements arranged one above another and shiftable with respect to one another. Two spindles arranged parallel to one another, each having a sliding block, are in working engagement with the link elements. One of the sliding blocks is connected via a lever mechanism to the first link element. The second sliding block engages into an elongated hole, arranged obliquely with respect to the spindle axis, of the second link element. An indication for the zero position of the specimen head is not provided here.

DE 196 04 001 C2 discloses a device for orienting a specimen head in a microtome. In this microtome, the specimen head is immovably connected to a ball joint for orientation. The ball joint has a ball, arranged between two ball half-shells, that is connected, for separate X-Y orientation of the specimen head, to a universal joint arranged inside the two ball half-shells. The universal joint has two handles, arranged perpendicular to one another, each having a threaded spindle. The threaded spindles are mounted rotatably in the ball half-shell and are each equipped with a nut. The nuts are each immovably connected to a pin, and the pins engage into two elongated holes, arranged perpendicular to one another, of the universal joint. A rotational motion at the handles is transferred via the threaded spindles to the nuts and the pins. The longitudinal motion of a pin is transferred to the universal joint, so that the specimen holder is pivoted or tilted in the spatial direction.

This device has proven successful in practical use, but is not equipped with any indication for recognition of the zero position of the specimen holder. As a result of the very small maximum pivot angle ($\leq 8°$), however, it is sometimes very difficult to align the sample accurately onto the cutting knife and to recognize the zero position, i.e. the location between two end positions of the nut.

SUMMARY OF THE INVENTION

It is therefore the object of the present invention further to develop the known device for orienting a specimen head for a microtome and to equip it with an indication for signaling the position of the specimen head.

The invention achieving this object is characterized in that an indication for signaling the position of the orientable sample holder is provided on the microtome, and is connected directly to the drive system for moving the sample holder. The drive system encompasses a rotatably mounted spindle and a nut running on the spindle. The nut is equipped with a position element identifying the zero position, and an indicating element is associated with that position element. The indication is thus derived directly from a position element of the drive.

In a development of the invention, the position element is embodied mechanically. Cams, lugs, levers, or grooves can be used here, for example, as mechanical elements together with the nut.

In an alternative embodiment of the invention, the position element is embodied as the reflector of a light barrier that, for example, can be adhesively bonded directly on the nut. The position on the microtome of the nut, and of the orientable specimen holder, can thus be transferred in non-contact fashion to the indicating element.

In a development of the invention, a transfer means, for transferring the position of the nut on the spindle to the indicating element, is associated with the position element. The transfer means constitutes the connecting structure between the position element on the nut and the indicating element on the housing.

In a development of the invention, the transfer means is embodied mechanically. Cams, lugs, levers, or grooves can be used here, for example, as mechanical elements together with the nut.

In an alternative embodiment of the invention, the transfer means is embodied either as an electrical switch that is actuated by a mechanical position element, or as a light barrier. Electrical and/or acoustic indications can then be controlled with both electrical transfer elements.

In a development of the invention, the indicating means is embodied mechanically for signaling the specimen position. It has proven advantageous in this context to embody the mechanical indicating means as a longitudinally movable indicating pin projecting out of the housing. The indicating means can, of course, also be embodied as a rotatable disk and be arranged on the housing.

In a further embodiment of the invention, the indicating means is embodied electrically and has, for example, an acoustic and/or optical indication.

In a development of the invention, a lever mounted in rotationally movable fashion is associated, as an element of the transfer means, with the cam arranged on the nut. One end of the lever has a rotary bearing, and an indicating pin is arranged as the indicating means at the other end of the lever.

In a further embodiment of the invention, a plunger is provided on the lever. Both the cam on the nut and the plunger on the lever carry a respective prismatic attachment having a tip.

In an advantageous development of the invention, the two oppositely located tips of the prismatic attachments (of the cam and plunger) define the sample orientation zero position. When the two tips are located directly opposite one another, the initial position or zero position of one axis of the sample holder has been reached. This embodiment also has the advantage that the mechanical parts enter into a working engagement only in this specific position, thus minimizing mechanical wear due to components rubbing against one another.

In a development of the invention, the indicating pin is arranged in the housing in such a way that it projects out of the housing when the sample holder is in the zero position. It has proven advantageous in this context to equip the periphery of the indicating pin with a signal color so that, for example, the zero position of the sample holder can thereby be unequivocally signaled.

In a further embodiment of the invention, the head of the indicating pin as well as the housing are configured in the same color. The result is that the housing and the indicating pin recessed into the housing, constitute a uniform surface with no color contrast.

BRIEF DESCRIPTION OF THE DRAWINGS

The invention will be explained in more detail with reference to an exemplary embodiment, with the aid of the schematic drawings in which.

DETAILED DESCRIPTION OF THE INVENTION

Figure 1:
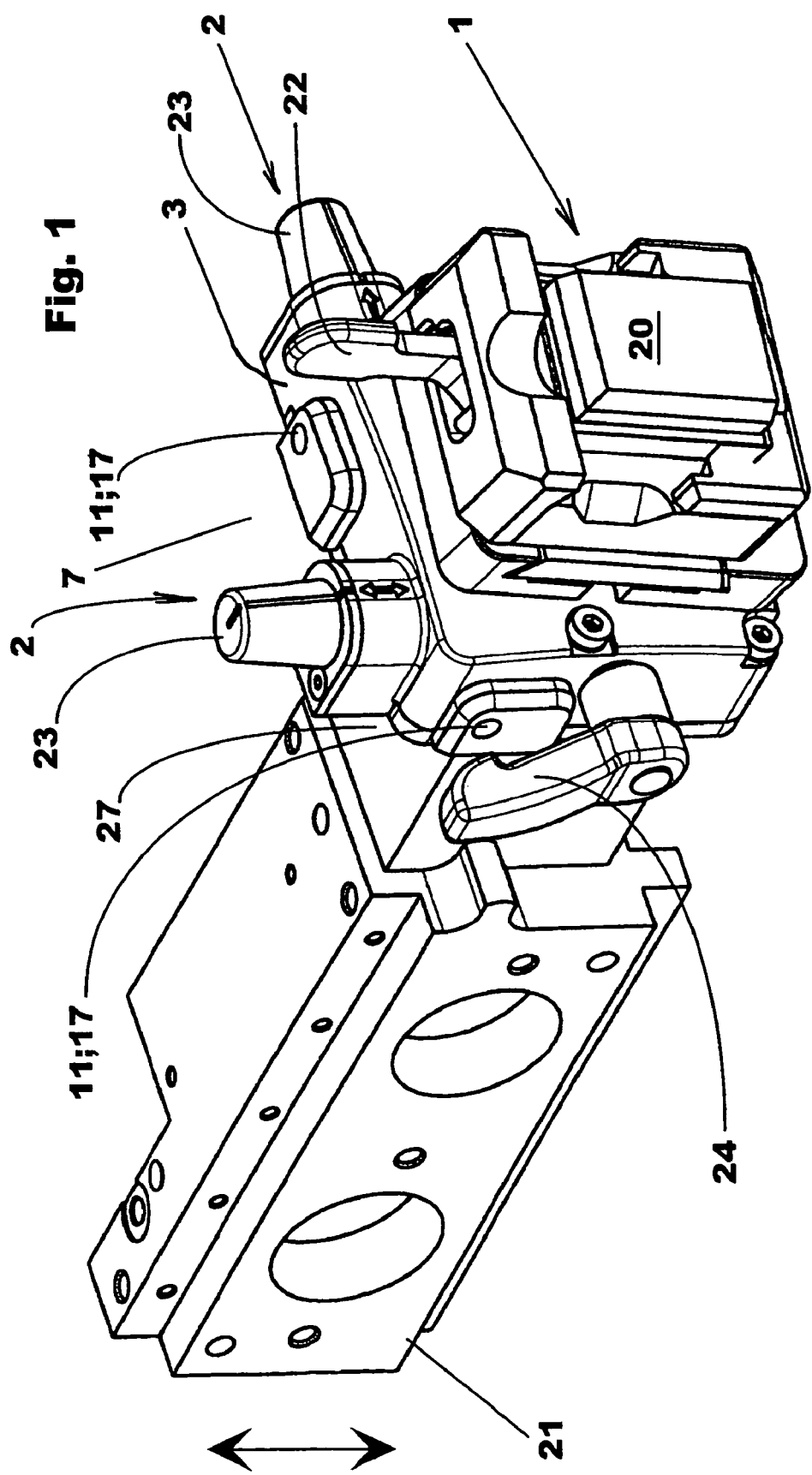
FIG. 1 is a view of the orientable sample holder with a sample.

FIG. 1 is a view of the orientable sample holder 1 with a sample 20. Sample holder 1 is equipped with a clamping lever 22 for immobilizing sample 20. Associated with sample holder 1 is a drive system 2 that is accommodated in a housing 3. Drive system 2 is equipped with two rotary knobs 23 arranged perpendicular to one another. With the two rotary knobs 23, sample holder 1 can be tilted separately in the X and the Y direction. The corresponding displacement axes X and Y are identified by the double arrows in the vicinity of rotary knobs 23.

Housing 3 is connected to a specimen carriage 21 via a displacement carriage 27, and can be shifted laterally on specimen carriage 21 using displacement carriage 27. Provided on housing 3 in order to immobilize this shift is a locking lever 24 with which housing 3 can be immobilized to prevent unintentional displacement.

Also provided on housing 3 are indicating means 7 for indicating the position of the orientable specimen holder 1. Indicating means 7 is embodied here as including indicating pin 11. Indicating pin 11 is equipped with a head 17 of the same color as the housing.

The relative motion between the cutting knife (not depicted) of a microtome and the sample to be cut is generated by way of specimen carriage 21, which is movable in the double-arrow direction.

Figure 2:
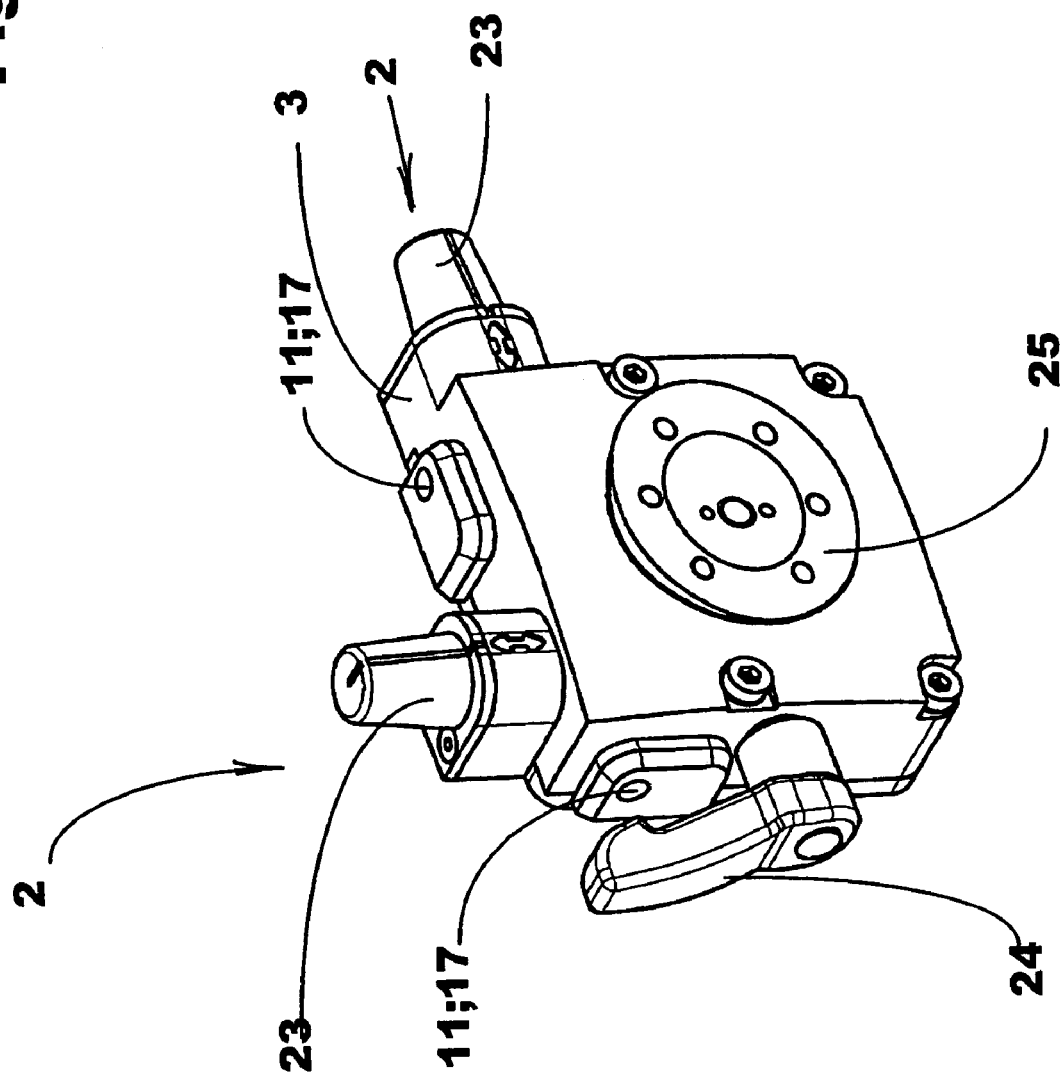
FIG. 2 is a view of the drive system arranged in a housing.

FIG. 2 is a view of housing 3 for drive system 2, having a ball piece 25. Ball piece 25 is displaceable separately in the X and the Y direction using drive system 2, and serves to secure the sample holder (not depicted here).

Figure 3:
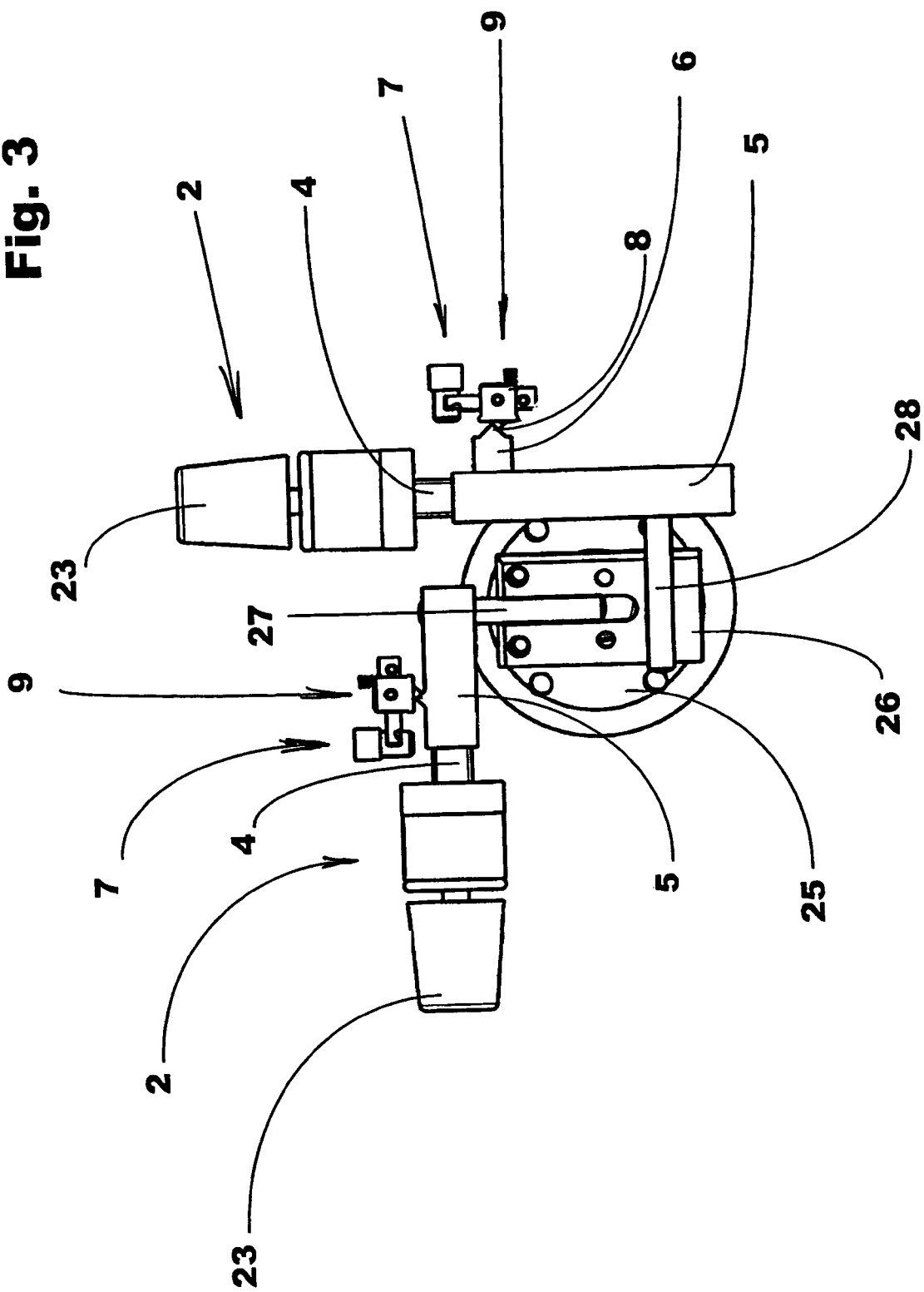
FIG. 3 is a sectioned depiction of the drive system with the sample holder outside the zero position.
Figure 5:
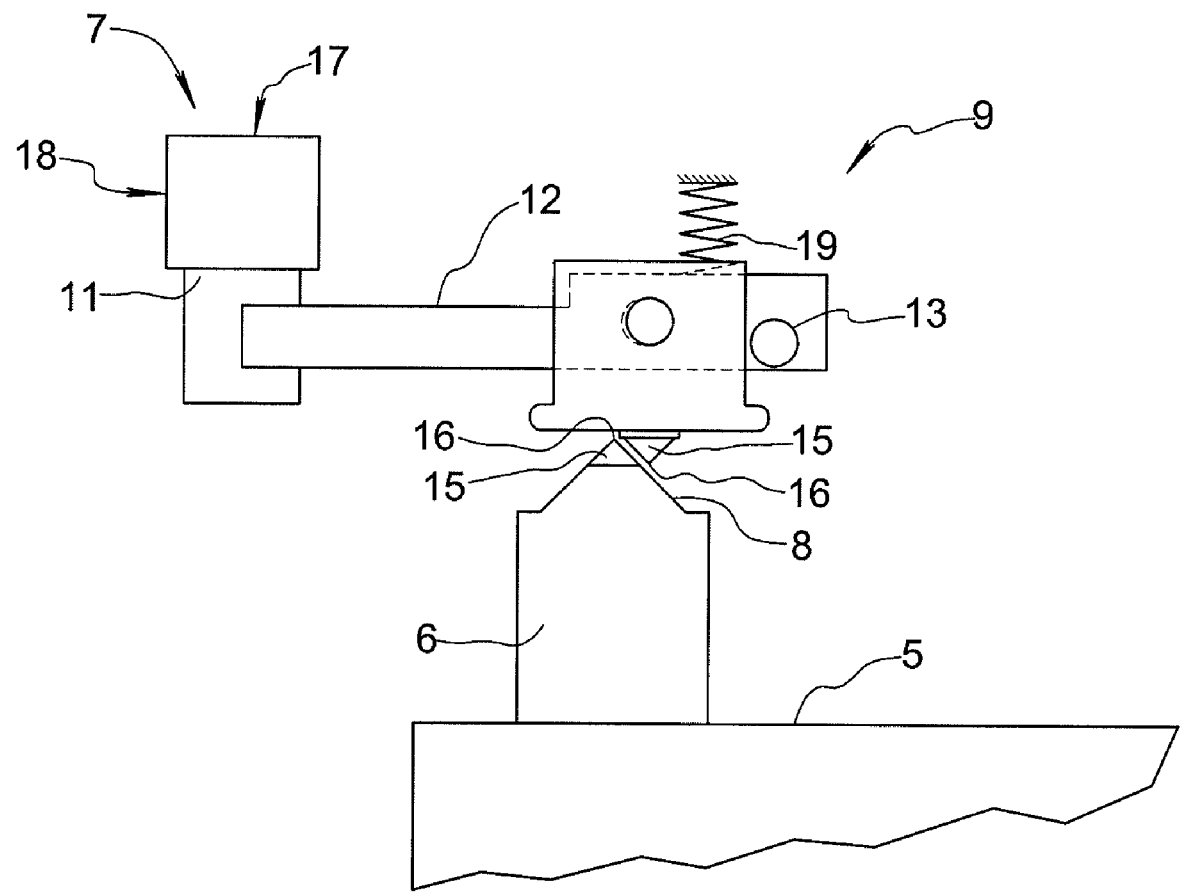
FIG. 5 is a view of a transfer means, a position element, and an indicating means formed in accordance with an embodiment of the present invention.

FIG. 3 is a sectioned depiction of drive 2, with a spindle 4, a nut 5 running on spindle 4, rotary knob 23 for moving spindle 4, and position element 6 connected to nut 5. A transfer means 9 having an attachment 15 is associated in oppositely located fashion with position element 6. Transfer means 9 is connected to an indicating means 7 in order to signal the position of the sample holder. Transfer means 9, position element 6, and indicating means 7 may also be seen in FIG. 5.

A motion pin 27, 28 of a universal joint 26 is connected to nut 5. Ball piece 25 can be moved in the X and the Y direction using universal joint 26.

Figure 4:
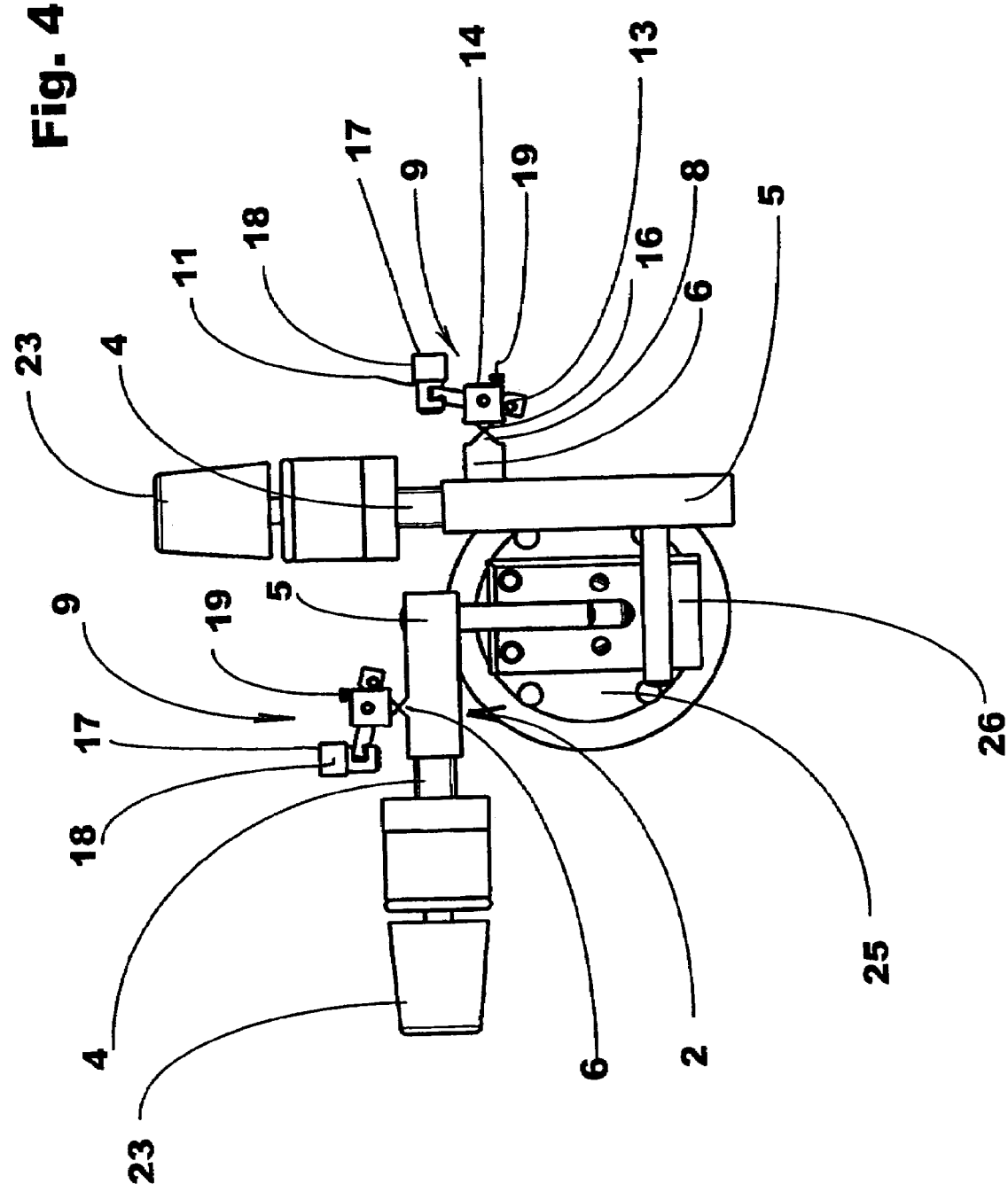
FIG. 4 is a sectioned depiction of the drive system with the sample holder in the zero position.

FIG. 4 is a further sectioned depiction of drive system 2 with spindle 4 and nut 5 running on spindle 4. A cam 8 is associated, as part of position element 6, with nut 5. Cam 8 carries a prismatic attachment 15 having a tip 16. Transfer means 9, located oppositely, is equipped with a lever 12 that has a compression spring 19 associated with it and is equipped at its one end with a rotary bearing 13. At its other end, lever 12 is associated with indicating pin 11. Indicating pin 11 bears a signal color on its periphery 18.

Lever 12 carries a plunger 14 that includes a prismatic attachment 15 equipped with a tip 16. Upon rotation of spindle 4, nut 5 moves with cam 8 on spindle 4. When cam 8 and tip 16 of plunger 14 are located directly opposite one another, lever 12 is pivoted about rotary bearing 13 against the force of spring 19, and indicating pin 11 is moved out of the housing (not depicted here).

This position of indicating pin 11 corresponds to the zero position of the sample holder in the X or Y direction. An indicating pin 11 projecting only partly out of the housing signals that the position of the sample holder deviates only slightly from the zero position. An indicating pin 11 withdrawn completely into the housing signals a position of the same holder pivoted out of the zero position.

With the device described, it is thus possible to align the sample holder of a microtome separately in the X and/or Y direction by way of a drive-system connection, and to indicate the position of the sample holder.

PARTS LIST

1 Sample holder
2 Drive system
3 Housing
4 Spindle
5 Nut
6 Position element
7 Indicating means
8 Cam of 6
9 Transfer means
11 Indicating pin
12 Lever
13 Rotary bearing
14 Plunger
15 Attachment
16 Tip
17 Head of 11
18 Periphery of 11
19 Spring
20 Sample
21 Specimen carriage
22 Clamping lever
23 Rotary knob
24 Locking lever
25 Ball piece
26 Universal joint
27 Displacement carriage
28 Motion pin

What is claimed is:

1. A sample positioning device for a microtome comprising:
   a sample holder;
   a drive system connected to the sample holder for moving the sample holder, the drive system including a rotatably mounted spindle and a nut running along the spindle for applying force along a drive axis to move the sample holder through a range of positions;
   a position element mounted for travel with the nut;

an indicating means operatively associated with the position element for signaling a user that the sample holder is in a zero-position with respect to the range of positions associated with the drive axis; and a transfer means for connecting the position element to the indicating means when the sample holder is in the zero-position, wherein the transfer means mechanically connects the position element to the indicating means, and wherein the transfer means includes a plunger actuated by the position element when the sample holder is in the zero-position, and a pivotable lever connected to the plunger for rotation about a pivot point in response to actuation of the plunger, the lever being connected to the indicating means.

2. The device as defined in claim 1, wherein the position element and the plunger each carry a respective prismatic attachment having a tip.

3. The device as defined in claim 2, wherein the tips of the respective prismatic attachments are opposite one another when the sample holder is in the zero-position.

4. The device as defined in claim 1, wherein the transfer means includes an electrical switch.

5. The device as defined in claim 1, wherein the transfer means includes a light barrier.

* * * * *